(12) United States Patent
Gardner et al.

(10) Patent No.: US 7,454,002 B1
(45) Date of Patent: Nov. 18, 2008

(54) INTEGRATING PERSONAL DATA CAPTURING FUNCTIONALITY INTO A PORTABLE COMPUTING DEVICE AND A WIRELESS COMMUNICATION DEVICE

(75) Inventors: Deane Gardner, Cupertino, CA (US); Mitz Kurobe, Tokyo (JP)

(73) Assignee: SportBrain, Inc., Sunnyvale, CA (US)

( * ) Notice: Subject to any disclaimer, the term of this patent is extended or adjusted under 35 U.S.C. 154(b) by 26 days.

(21) Appl. No.: 09/757,241

(22) Filed: Jan. 8, 2001

Related U.S. Application Data

(63) Continuation-in-part of application No. 09/476,142, filed on Jan. 3, 2000, now abandoned.

(51) Int. Cl.
  *H04M 3/42* (2006.01)
  *H04B 1/034* (2006.01)
  *G01B 5/02* (2006.01)

(52) U.S. Cl. .................. 379/201.05; 455/100; 702/160

(58) Field of Classification Search ................. 600/300; 455/414.1, 403, 404.1, 412.2, 95, 91, 557, 455/556.2, 556.1, 100; 379/201.05
  See application file for complete search history.

(56) References Cited

U.S. PATENT DOCUMENTS

| | | | |
|---|---|---|---|
| 5,598,849 A | 2/1997 | Browne | 600/520 |
| 5,722,418 A | 3/1998 | Bro | 600/300 |
| 5,810,722 A | 9/1998 | Heikkila | 600/300 |
| 5,827,179 A | 10/1998 | Lichter et al. | 600/300 |
| 5,827,180 A | 10/1998 | Goodman | 600/300 |
| 5,891,042 A | 4/1999 | Sham et al. | 600/483 |
| 5,960,403 A | 9/1999 | Brown | 705/2 |
| 5,976,083 A | 11/1999 | Richardson et al. | 600/300 |
| 6,102,856 A | 8/2000 | Groff et al. | 600/301 |
| 6,132,337 A | 10/2000 | Krupka et al. | 482/8 |
| 6,135,951 A | 10/2000 | Richardson et al. | 600/300 |

(Continued)

FOREIGN PATENT DOCUMENTS

JP  05252068 A  *  9/1993

(Continued)

OTHER PUBLICATIONS

Doctors praise banned heart-fax device [online], [retrieved on Dec. 4, 2003]. Retrieved from the Internet <http://www.cnn.com/2003/HEALTH/12/04/heart.device.ap/index.html>.*

(Continued)

*Primary Examiner*—Curtis Kuntz
*Assistant Examiner*—Joseph T Phan
(74) *Attorney, Agent, or Firm*—Edell, Shapiro & Finnan, LLC

(57) ABSTRACT

In one embodiment, personal data capturing functionality is integrated into a wireless communication device or a portable computing device by incorporating one or more personal parameter receivers into the wireless communication device or the portable computing device. In another embodiment, personal data capturing functionality is integrated into a wireless communication device or a portable computing device by attaching a personal data capture device to the wireless communication device or the portable computing device. The personal data capture device is configured to receive personal data of a user and transmit the personal data to the wireless communication device or the portable computing device, either of which is capable of transmitting the personal data to a network server over a wireless network.

16 Claims, 7 Drawing Sheets

U.S. PATENT DOCUMENTS

| | | | |
|---|---|---|---|
| 6,252,883 B1* | 6/2001 | Schweickart et al. | 370/441 |
| 6,349,126 B2 | 2/2002 | Ogawa et al. | |
| 6,512,456 B1* | 1/2003 | Taylor, Jr. | 340/573.1 |
| 6,605,038 B1* | 8/2003 | Teller et al. | 600/300 |
| 6,696,956 B1* | 2/2004 | Uchida et al. | 340/573.1 |
| 6,997,852 B2 | 2/2006 | Watterson et al. | |
| 7,030,735 B2 | 4/2006 | Chen | |
| 7,062,225 B2* | 6/2006 | White | 455/41.2 |
| 7,063,665 B2 | 6/2006 | Hasegawa et al. | |
| 2001/0007825 A1* | 7/2001 | Harada et al. | 463/7 |
| 2002/0072932 A1* | 6/2002 | Swamy | 705/2 |
| 2006/0073807 A1* | 4/2006 | Baker | 455/405 |

FOREIGN PATENT DOCUMENTS

WO     WO 00/68913 A2 * 11/2000

OTHER PUBLICATIONS

PCT Search Report dated Apr. 9, 2001, 4 pages.

Huhn, M., "New Gadgets Get A Workout," [25 paragraphs] NYPOST.com [Online]. Available: http://www.nypost.com/technology/18546.htm.

Time, Inventions 2000, Phone-In Checkups, Available: http://www.sportbrain.com/AboutUs/images/ArticleTime.gif.

Wall Street Journal, WSJ.com, "The Pursuit of Happiness," [7 paragraphs] Available: http://www.sportbrain.com/AboutUs/images/ArticleWSJ_o.gif.

Fortt, J. (May 27, 2000) "Exercise Buff Strap On Latest In Workout Technology" [28 paragraphs] SiliconValley.com [Online]. Available: http://www.sjmercury.com/svtech/computing/center/sport052800.htm.

Huhn, M., "New Gadgets Get A Workout," [25 paragraphs] NYPOST.com [Online]. Available: http://www.nypost.com/technology/18546.htm, Dec. 21, 2000.

Time, Inventions 2000, Phone-In Checkups, Available: http://www.sportbrain.com/AboutUs/images/ArticleTime.gif, year 2000.

Wall Street Journal, WSJ.com, "The Pursuit of Happiness," [7 paragraphs] Available: http://www.sportbrain.com/AboutUs/images/ArticleWSJ_o.gif, Feb. 9, 2001.

* cited by examiner

INTEGRATING PERSONAL DATA CAPTURING FUNCTIONALITY INTO A PORTABLE COMPUTING DEVICE AND A WIRELESS COMMUNICATION DEVICE

This application is a continuation-in-part of application Ser. No. 09/476,142, filed Jan. 3, 2000 now abandoned.

BACKGROUND OF THE INVENTION

1. Field of the Invention

The present invention relates to personal data capturing systems. More particularly, the present invention relates to integrating personal data capturing functionality into portable computing devices and wireless communication devices.

2. Background Information

Physical fitness is known to benefit people in many different areas, including improved flexibility and range of motion, increased muscular strength and cardiovascular fitness, body fat loss and increased stamina. Physical exercise helps maintain good health, increases energy, reduces stress and improves physical appearance. However, in order to gain the benefits of regular physical exercise, the users need to be able to conveniently access information concerning their exercise level and receive a feedback concerning their fitness activity.

Conventional devices are known for providing such information to the users. For example, U.S. Pat. No. 5,810,722 describes a device for measuring heartbeat rate. An athlete or a person engaged in fitness training may wear the device on the breast or the wrist. The device measures the heartbeat rate based on skin contact and allows the user to read the result from a display provided in the casing of the device. U.S. Pat. No. 5,891,042 describes a fitness monitoring device which includes an electronic pedometer integrated together with a wireless heart rate monitor. The device may be secured to the user's belt or waist band. The device receives electrical signals from a telemetric transmitter unit arranged on the user's skin adjacent to his heart and calculates the heart rate. The device is also configured to detect the user's body motion at each step for performing step counting. The user can read the results from a display provided in the casing of the device. The display includes an alpha/numeric display portion and a heart rate monitoring icon. These prior art devices, however, merely allow the users to see the physiological information concerning their exercise level. They do not provide any processed feedback to the users. In addition, these devices can be cumbersome to wear and they force the users to monitor their own activity, thereby interfering with their focus on physical exercise.

Therefore, what is required is a portable device which will provide the users with convenient access to information concerning their exercise level and will effectively assist the users in their fitness activity.

SUMMARY OF THE INVENTION

The present invention relates to various aspects for integrating personal data capturing functionality into a wireless communication device and a portable computing device. According to one aspect of the present invention, an exemplary wireless communication device comprises one or more personal parameter receivers to receive personal data of a user, a microprocessor coupled to the personal parameter receivers, and a memory coupled to the microprocessor to store the personal data. The microprocessor is configured to transmit the personal data from the memory to a network server via a wireless network. In one embodiment, an exemplary portable computing device includes similar components, thereby integrating personal data capturing functionality into the portable computing device.

According to another aspect of the present invention, personal data capturing functionality is integrated into a wireless communication device by attaching a personal data capture device to the wireless communication device. The personal data capture device is configured to receive personal data of a user and transmit the personal data to the wireless communication device, which is capable of transmitting the personal data to a network server over a wireless network. In one embodiment, personal data capturing functionality is integrated into a portable computing device by attaching a personal data capture device to the portable computing device. The personal data capture device is configured to receive personal data of a user and transmit the personal data to the portable computing device, which is capable of transmitting the personal data to a network server over a wireless network.

Other features of the present invention will be apparent from the accompanying drawings and from the detailed description that follows.

BRIEF DESCRIPTION OF THE DRAWINGS

The present invention is illustrated by way of example and may be better understood by referring to the following description in conjunction with the accompanying drawings, in which like references indicate similar elements and in which.

DETAILED DESCRIPTION OF AN EMBODIMENT OF THE PRESENT INVENTION

Figure 1:
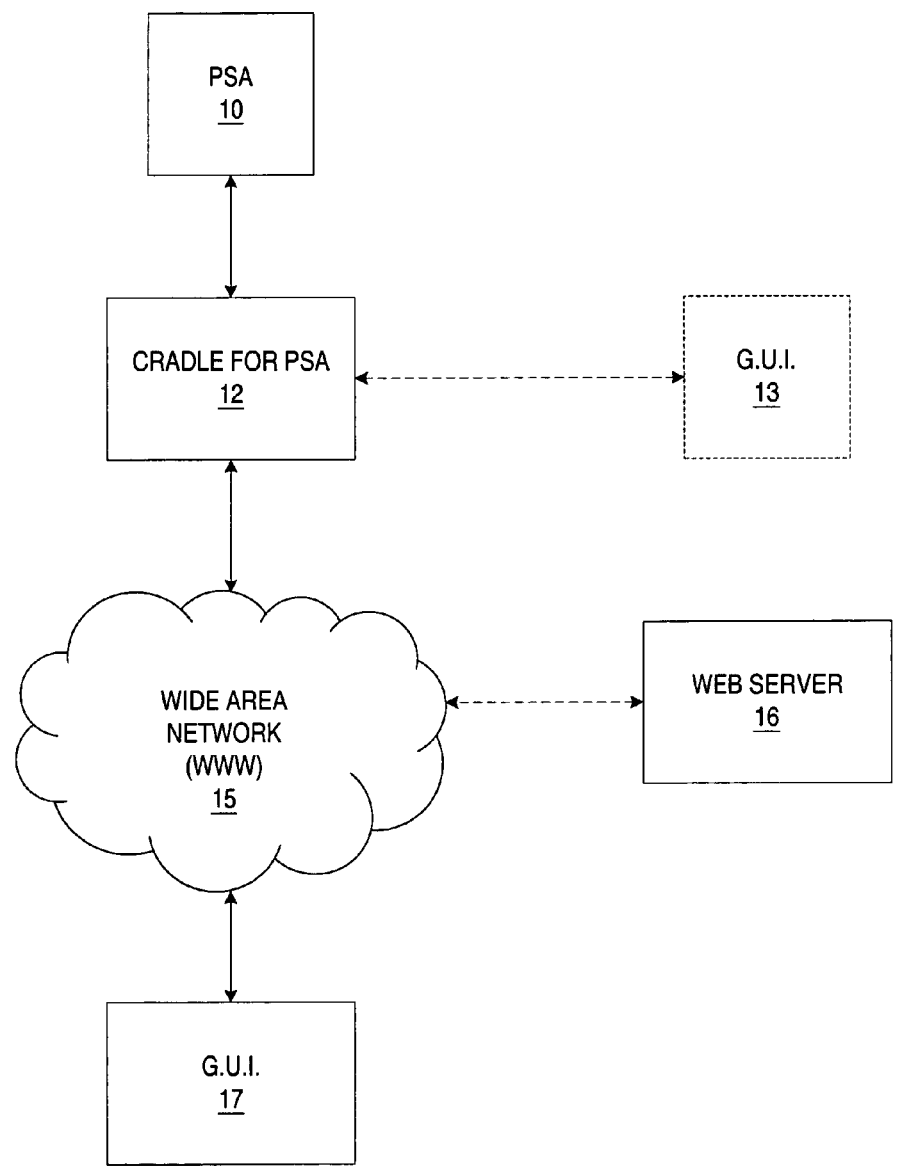
FIG. 1A is a block diagram of one embodiment for a network architecture.
FIGS. 1B and 1C are block diagrams of two alternative embodiments of a system for integrating personal data capturing functionality into a portable computing device and a wireless communication device.

The present invention relates to various aspects for integrating personal data capturing functionality into a wireless communication device and a portable computing device. In the following detailed description of the present invention, numerous specific details are set forth in order to provide a thorough understanding of the present invention. However, it will be apparent to one skilled in the art that the present invention may be practiced without these specific details. In some instances, well-known structures and devices are shown in block diagram form, rather than in detail, in order to avoid obscuring the present invention.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of processing blocks leading to a desired result. The processing blocks are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

Referring now to FIG. 1A, a block diagram of one embodiment for a network architecture is illustrated. In this embodiment, portable sports appliance (PSA) 10 is coupled to cradle 12. PSA 110 may be used to monitor and store physical and biometrical parameters of its user. In this embodiment, PSA 10 is a portable device. However, it will be recognized by one of ordinary skill in the art that a stationary device or a device included in some other device or equipment may be used with this invention without loss of generality. PSA 10 may be used by any person. For example, PSA 10 may be used by a person engaged in fitness activity, a professional athlete during exercise, or an employee wishing to know how his stress level changes during the day. The operation of PSA 10 and its functions will be described in more details below.

Cradle 12 is used to upload data from personal data capture device 10 to network 15. In one embodiment, cradle 12 may resemble a support element for a telephone receiver or handset. Cradle 12 may include a modem to transmit data over telephone lines and may be configured to provide two-way connection to wide area network 15. In one embodiment, placing personal data capture device 10 in cradle 12 may trigger an automatic dialing of a telephone number of server 16. When the telephone line is free, data from personal data capture device 10 may then be transmitted to server 16 through wide area network 15.

Alternatively, the data may be transmitted from personal data capture device to server 16 using a wireless transmitter. That is, cradle 12 is not used, and the data is transmitted over a wireless carrier. It should be understood by one of ordinary skill in the art that various ways of transmitting data from PSA 10 to server 16, other than those described above, may be used with this invention without loss of generality.

Cradle 12 may be used with more than one PSA 10. For example, if each family member has his or her own PSA 10, cradle 12 may be shared by all family members. Personal data of each family member is then uploaded to server 16 at various points of time. Server 16 may receive personal data from numerous PSA users. This personal data may then be processed by third parties that may provide feedback information to those PSA users who subscribe for this service.

In one embodiment, server 16 is coupled to wide area network 15. Wide area network 15 may include, for example, the Internet, America On-Line™, CompuServe™, Microsoft Network™, or Prodigy™. In addition, wide area network 15 may include, for example, conventional network backbones, long-haul telephone lines, Internet service providers, or various levels of network routers. Using conventional network protocols, server 16 may communicate through wide area network 15 to a plurality of clients.

In one embodiment, server communicates to clients 13 and 17. Clients 13 and 17 represent any device that may enable user's access to data. For simplicity, FIG. 1A shows only two clients, client 13 and client 17, that can communicate to server 16. However, it will be recognized by one of ordinary skill in the art that server 16 may communicate to a various number of clients and that a wide variety of client devices may be used with this invention without loss of generality. Such devices may include, for example, a conventional computer system, a network computer or thin client device (e.g., WebTV Networks™ Internet terminal or Oracle™ NC), a laptop or palmtop computing device (e.g., Palm Pilot™), a digital consumer device (e.g., a digital TV, a digital camcorder, or a "kitchen" computer"), etc. In one embodiment, clients 13 and 17 may have a Graphical User Interface (GUI) to allow users to access data. A GUI is a graphics-based user interface that incorporates icons, pull-down menus and a mouse. GUIs may include, for example, Microsoft Windows, Apple Macintosh, UNIX Motif, or UNIX OPENLOOK.

Clients 13 and 17 may be connected to server 16 in various ways. In one embodiment, clients 13 and 17 may be connected to server 16 through wide area network 15. Client 17 may represent client devices of third parties, e.g., health and fitness specialists, who access personal data of subscribers on server 16 via wide area network 15 to generate feedback information to subscribers. Client 13 may represent client devices of subscribers who access the generated feedback information via wide area network 15. In this embodiment, client 13 is connected to cradle 12 which provides two-way connection with wide area network 15. However, it will be understood by one of ordinary skill in the art that client 13 does not need to be connected to cradle 12. Instead, client 13 may use the same connection means as client 17.

In an alternate embodiment (not shown in FIG. 1A), a client, such as client 13 or client 17, may be directly connected to server 16 or through a modem in a conventional way. When connected to wide area network 15, clients 13 and 17 may be connected directly to wide-area network 15 through direct or dial up telephone or other network transmission line. Alternatively, clients 13 and 17 may be connected to wide-area network 15 using a modem pool. A conventional modem pool may allow a plurality of clients to connect with a smaller set of modems in modem pool for connection to wide-area network 15. In yet another network typology, wide-area network 15 may be connected to a gateway computer, which may be used to route data to clients through a local area network. In this manner, clients can communicate with each other through a local area network (LAN) or with server 16 through a gateway and wide-area network 15. Alternatively, LAN may be directly connected to server 16 and clients may be connected through LAN. For example, subscribers' personal data may be processed by a company employing fitness instructors, athletic trainers, physicians and other heath and fitness specialists. Such a company may use LAN topology for providing internal communication between its employees. LAN may then be connected to server 16 through wide area network 15 for allowing communication between subscribers and health and fitness specialists.

Using one of a variety of network connection means, server computer 16 may communicate with clients 15 using conventional means. In one embodiment, a server computer 16 may operate as a web server if the World-Wide Web (WWW) portion of the Internet is used for wide area network 15. Using the HTTP protocol and the HTML coding language across a network, web server 16 may communicate across the World-Wide Web with clients 13 and 17. In this configuration, clients 13 and 17 may use a client application program known as a web browser such as the Netscape™ Navigator™ published by Netscape Corporation of Mountain View, Calif., the Internet Explorer™ published by Microsoft Corporation of Redmond, Wash., the user interface of America On-Line™, or the web browser or HTML translator of any other conventional supplier. Using such conventional browsers and the World-Wide Web, clients 13 and 17 may access graphical and textual data or video, audio, or tactile data provided by web server 16. Conventional means exist by which clients 13 and 17 may supply information to web server 16 through the World-Wide Web 15 and the web server 16 may return processed data to clients 13 and 17.

Figure 1B:
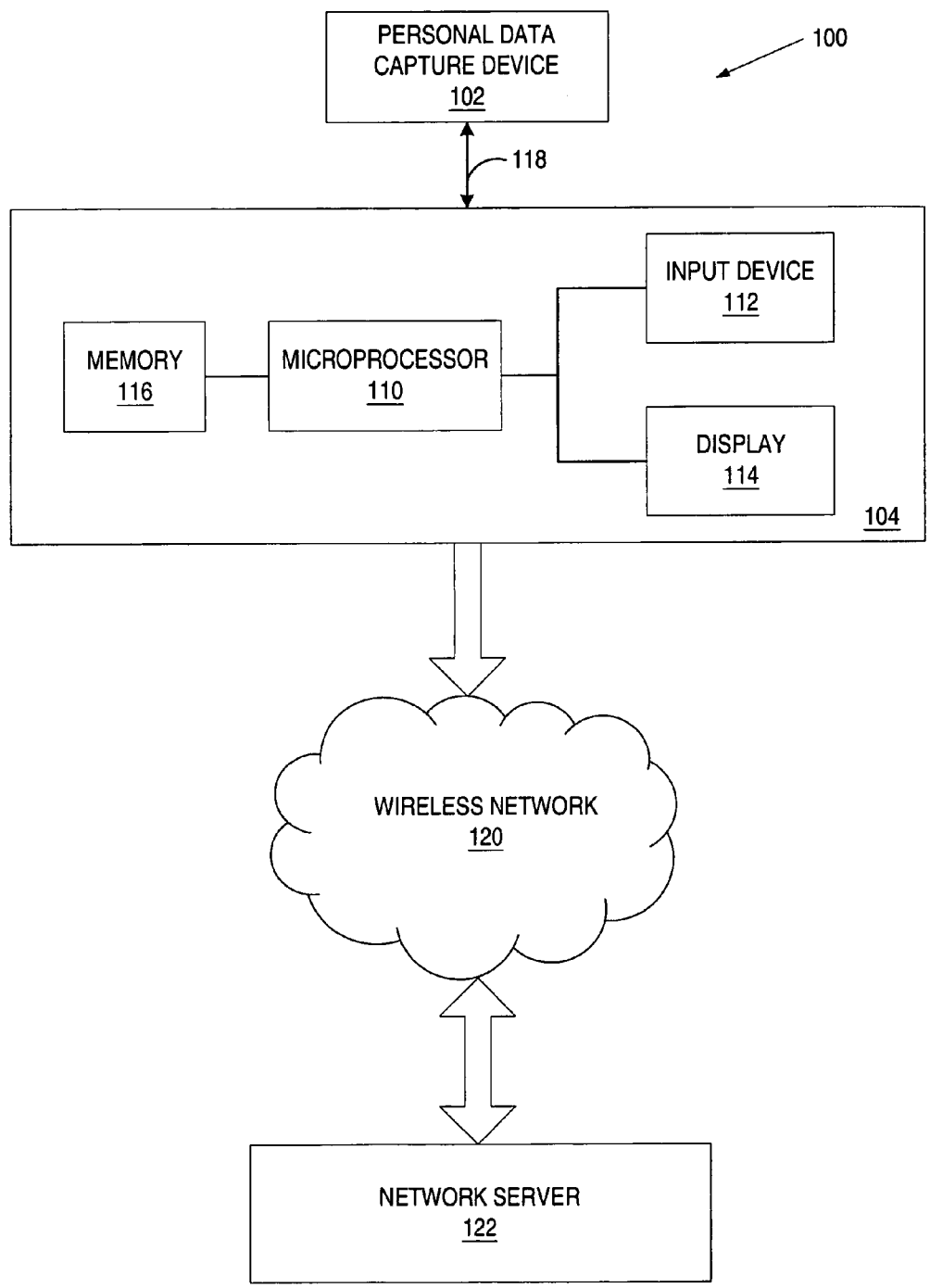
Figure 1C:
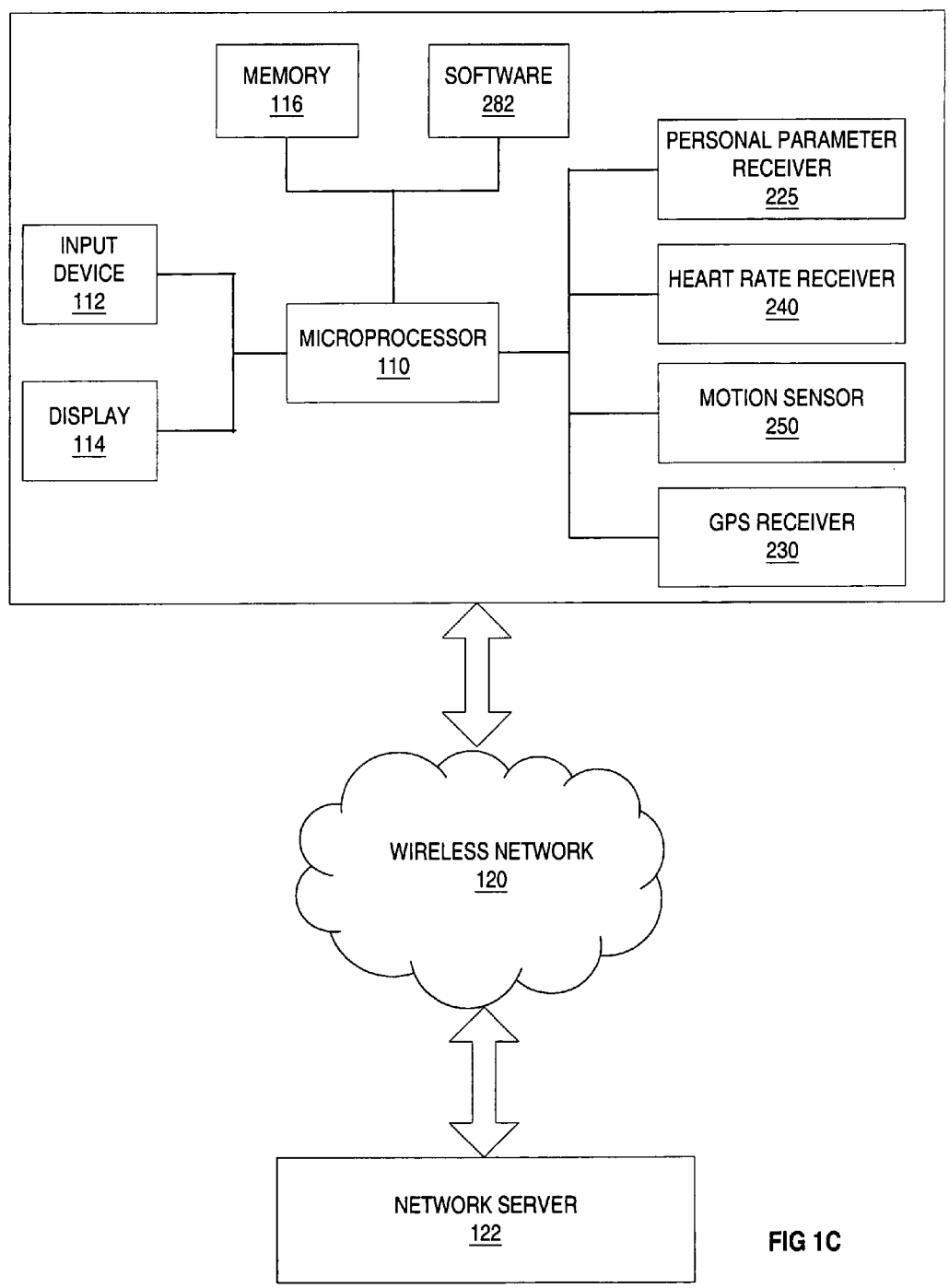

FIGS. 1B and 1C are block diagrams of two alternative embodiments of a system for integrating personal data capturing functionality into a portable computing device and a wireless computing device. Referring to FIG. 1B, a system 100 provides personal data capturing functionality using a personal data capture device 102. The personal data capture device 102 is attachable to a device 104. In one embodiment, the device 104 is a wireless communication device such as, for example, a radiotelephone, a cellular phone, a pager, etc. In another embodiment, the device 104 is a portable computing device such as, for example, a personal digital assistant (PDA), a palmtop computer, etc. In yet another embodiment, the device 104 is a combination of a wireless communication device and a portable computing device (e.g., a combination of a PDA and a cellular phone).

In one embodiment, an expansion slot in the device 104 may be used to attach the personal data capture device 102 to the device 104. For instance, some PDAs (e.g., a Handspring Visor™) are designed with expansion slots for adding software and hardware modules. Alternatively, any other means known in the art may be used to attach the personal data capture device 102 to the device 104. When attached, the personal data capture device 102 can communicate with the device 104 using an interface such as, for example, a bus 118. The bus 118 can be an inter-integrated circuit (I2C) bus or any other conventional bus suitable for transferring data between electronic devices.

Figure 2:
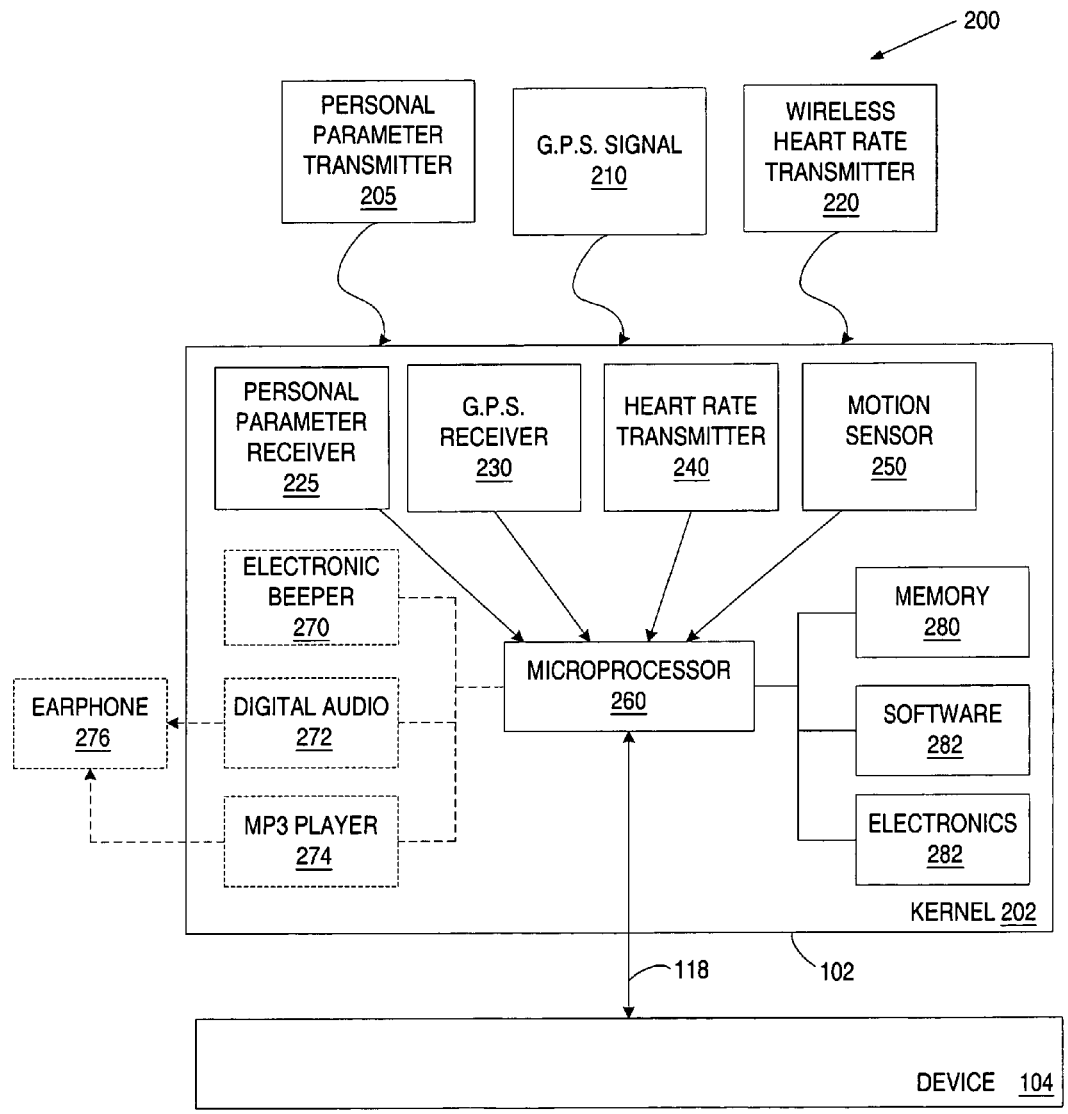
FIG. 2 is a block diagram of one embodiment for a personal data capture device.

An exemplary personal data capture device will now be described in greater detail. FIG. 2 is a block diagram of one embodiment for a personal data capture device 102. The personal data capture device 102 includes a global positioning system (GPS) signal receiver 230 which receives GPS signals 210. GPS signals 210 may include three-dimensional positional information and velocity of the user when the user is walking or running, or is engaged in some other relevant activity. The personal data capture device 102 may also include a motion sensor 250 which may improve the accuracy of the above information or substitute it when a GPS signal 210 is interrupted. In addition, the personal data capture device 202 may include a heart rate receiver 240 which receives heart beat rate from a wireless heart rate transmitter 220. Various other sources may provide signals to the personal data capture device 102. A personal parameter transmitter 205 represents a wide variety of signals that may be received by various personal parameter receivers 225 included in the personal data capture device 102. For example, a blood pressure meter, a glucose meter, exercise equipment such as treadmills and stationary bikes, or any other device or equipment can transmit data to the personal data capture device 102 which will receive it using a corresponding personal parameter receiver 225. In one embodiment, the heart rate receiver 240, the GPS receiver 230, the motion sensor 250, and the personal parameter receiver 225 are included in one receiver, e.g., a personal parameter receiver 225. It will be understood by one of ordinary skill in the art that all of the receivers described above or any combination of them may be included in the personal data capture device 102 without loss of generality.

The personal data capture device 102 further includes a microprocessor 260 which is coupled to a memory 280, a software program 282, and electronics 284. Upon receiving a signal, any of the receivers 225 through 250 outputs data to the microprocessor 260. The microprocessor 260 stores this data in the memory 280. Software 282 is stored in a machine-readable medium that is capable of storing or encoding a sequence of instructions for execution by the microprocessor 260 and that causes the microprocessor 260 to perform any one of the methodologies of the present invention. Software 282 may also reside, completely or at least partially, within the memory 280 and/or within the microprocessor 260, or in a machine-readable medium of any device coupled to personal data capture device 200, such as the device 104 or a network server 122. The term "machine-readable medium" shall accordingly be taken to include, but not be limited to, solid-state memories, optical and magnetic disks, and carrier wave signals.

In one embodiment, the personal data capture device 102 may include an electronic beeper 270 for providing audio signals related to the personal data. For example, the electronic beeper 270 can be set to signal low and high heart rate target limits, low and high pace limits, low and high weight limits, etc. In addition to the electronic beeper 270, the personal data capture device 102 may include a digital audio 272 to provide more detailed feedback. The digital audio 272 may be configured to provide various real time information (e.g., a distance or average speed) related to personal parameters transmitted to the personal data capture device 102. The personal data capture device 102 may also include a digital audio player such as an MP3 player 274 to play digital recordings. In one embodiment, the real time information generated by the digital audio 272 and/or digital recordings played by the MP3 player 274 may be communicated to the user by an earphone 276 coupled to the digital audio 272 and/or the MP3 player 274. It will be understood by one of ordinary skill in the art that any combination of the personal data receivers 225 through 250 and the audio signal generators 270 through 276 may be used with the personal data capture device 102 without loss of generality.

In one embodiment, a panic button is coupled to microprocessor 260. In this embodiment, software 282 analyzes personal data in memory 280. If the personal data includes a parameter that is below or exceeds a certain panic parameter (e.g., heart rate is too low or too high), software 282 may cause microprocessor 260 to invoke the panic button. The panic button may then produce a panic signal to a satellite page service or a cellular service. In one embodiment, the panic parameters may be set or updated from the user's web site and transferred to memory 280 over the wide area network. In alternate embodiments, the panic parameters may be set or updated by health or fitness specialists in network server 122 or programmed during the manufacture of personal data capture device 102.

When the personal data capture device 102 is attached to the device 104, the microprocessor 260 transmits portions or all of the personal data stored in the memory 280 to the device 104 via the bus 118. In one embodiment, the microprocessor 260 transmits the personal data to the device 104 periodically. Alternatively, the personal data capture device 102 may transmit the personal data upon receiving a request for information from the device 104.

Returning to FIG. 1B, the device 104 (i.e., a wireless communication device, a portable computing device, or a combination of a wireless communication device and a portable computing device) includes a microprocessor 110 which receives the personal data from the personal data capture device 102, stores the personal data in memory 116, and transmits any portion of the personal data from the memory 116 to a network server 122 over a wireless network 120. The wireless network 120 may be a fixed wireless network, a mobile wireless network (e.g., a cellular phone network), a wireless local area network (WLAN), an infrared (IR) wireless network, etc. In one embodiment, the microprocessor 110 transmits the personal data to the network server 122 periodically. Alternatively, the microprocessor 110 may be coupled to an input device 112 which allows the user to request transmission of the personal data to the network server 122. In one embodiment, the microprocessor 110 is also coupled to a display 114 which presents various information related to the user's personal data. For instance, a cellular phone display may display the user's heart rate, the number of steps counted during the user's fitness activity, the amount of calories burned by the user during the user's fitness activity, etc. In one embodiment, the device 104 requests the information to be displayed from the personal data capture device 102. Alternatively, the device 104 processes the personal data stored in its memory 116 to generate the information to be displayed. In one embodiment, the display 114 may be used to view any Internet information using a wireless application protocol (WAP) and a microbrowser.

In one embodiment, the network server 122 is a web server providing services to users (also referred to herein as subscribers). The services may include, for example, providing feedback related to the user's health and fitness activities from various specialists, such as fitness instructors, athletic trainers, diet or nutrition specialists, physicians, or any other fitness or health specialists. This feedback and other information related to the personal data (e.g., various graphs, tables, map overlays, progressive charts, and comparisons with data of other users) are displayed to the user on a user's personal web site. The user's web site may be accessed by the user from any client device (e.g., a personal computer) or the display 114 of the device 104.

FIG. 1C is a block diagram of an alternative embodiment of a system for integrating personal data capturing functionality into a portable computing device and a wireless computing device. In this embodiment, the personal data capturing functionality is provided by incorporating components of the personal data capture device into a device 150 which may be a wireless communication device, a portable computing device, or a multi-purpose device combining a wireless communication device and a portable computing device. Specifically, the device 150 may include a GPS signal receiver 230, a motion sensor 250, and a heart rate receiver 240. In addition, the device 150 may include a personal parameter receiver 225 receiving personal data from various other sources as described above. In one embodiment, the heart rate receiver 240, the GPS receiver 230, the motion sensor 250, and the personal parameter receiver 225 are included in one receiver, e.g., a personal parameter receiver 225. It will be understood by one of ordinary skill in the art that all of the receivers described above or any combination of them may be included in the device 150 without loss of generality.

The device 150 further includes a microprocessor 110 which is coupled to a memory 116 and a software program 282. Upon receiving a signal, any of the receivers 225 through 250 outputs data to the microprocessor 110. The microprocessor 110 stores this data in the memory 116. Software 282 is stored in a machine-readable medium that is capable of storing or encoding a sequence of instructions for execution by the microprocessor 110 and that causes the microprocessor 110 to perform any one of the methodologies of the present invention. Software 282 may also reside, completely, or at least partially, within the memory 116 and/or within the microprocessor 110, or in a machine-readable medium of any device coupled to the device 150, such as network server 122.

The microprocessor 110 is configured to transmit the personal data from the memory 116 to the network server 122 over the wireless network 120 in the same manner as described above in conjunction with FIG. 1B. In one embodiment, the device 150 includes an input device 112 coupled to the microprocessor 110 for receiving input information from the user. For instance, the user may use the input device 112 to request transmission of the personal data to the network server 122.

In one embodiment, the device 150 further includes a display 114 for displaying various information pertaining to the user's personal data, e.g., the user's heart rate, the number of steps counted during the user's fitness activity or during the day, the amount of calories burned by the user during the user's fitness activity or during the day, etc. In one embodiment, the display 114 can be also used to view any Internet information including feedback information generated by the network server 122 as described in greater detail above in conjunction with FIG. 1A.

It should be noted that various other components including other components of the personal data capture device 102 may be incorporated into the device 150. For instance, the device 150 may include the electronic beeper 270, the digital audio 272, etc.

Figure 3:
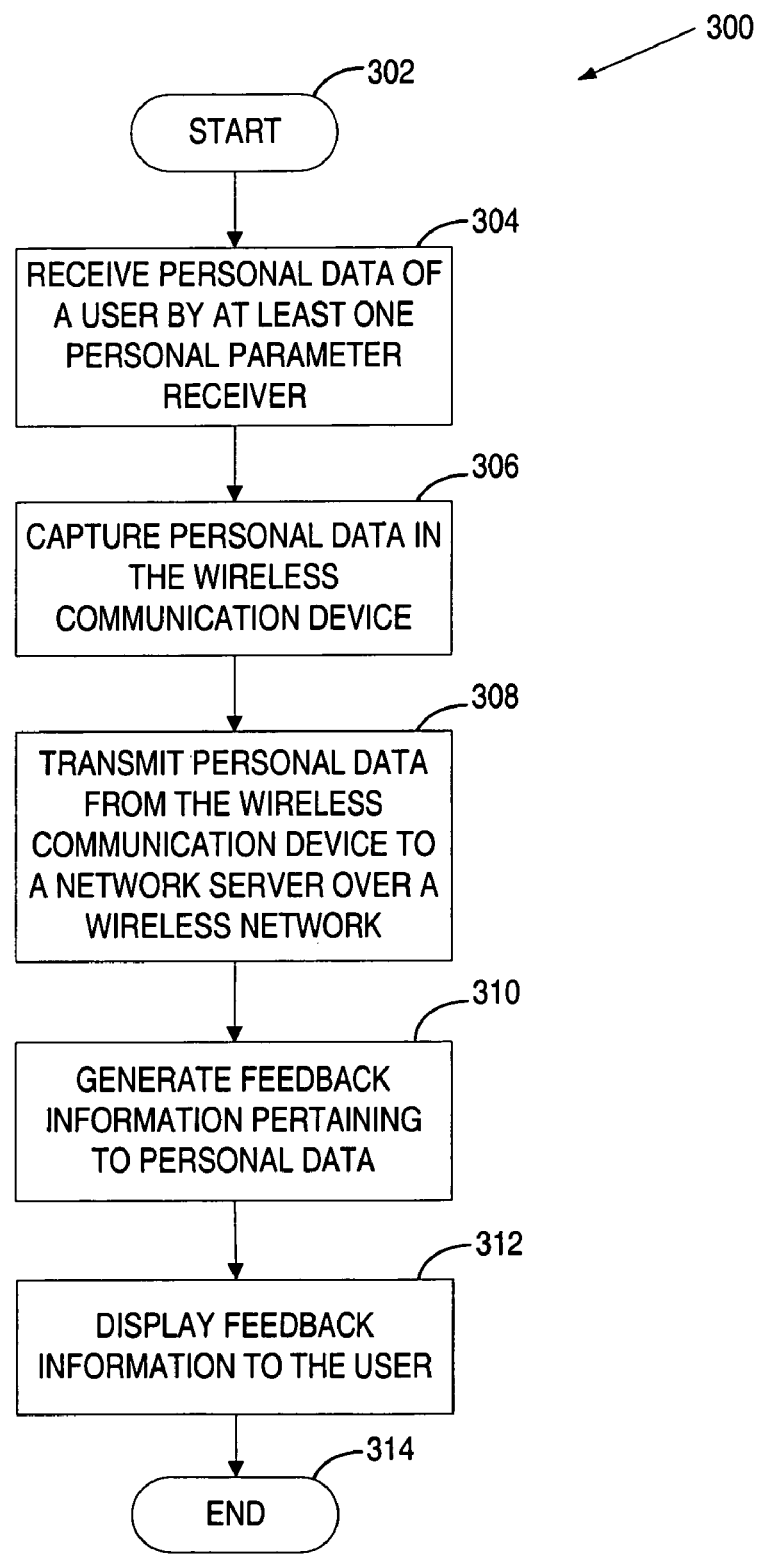
FIG. 3 is a flow diagram of a method for integrating personal data capturing functionality into a wireless communication device, according to one embodiment of the present invention.

FIG. 3 is a flow diagram of a method for integrating personal data capturing functionality into a wireless communication device, according to one embodiment of the present invention. At processing block 304, user's personal data is received by one or more personal parameter receivers. In one embodiment, the personal parameter receivers are contained in a separate personal data capture device which is attachable to a wireless communication device. Alternatively, the personal parameter receivers are a part of the wireless communication device. The wireless communication device may be, for example, a radiotelephone, a cellular phone, a pager, etc. In one embodiment, the wireless communication device is combined with a portable computing device (e.g., a combination of a PDA and a cellular phone). In one embodiment, the personal data includes physical data and biometrical parameters of the user.

At processing block 306, the personal data collected by the personal parameter receivers is captured in the wireless communication device. In one embodiment, in which the personal parameter receivers are a part of the wireless communication device, the personal parameter receivers directly output the personal data to a microprocessor which then stores it in memory. In an alternate embodiment, in which the personal parameter receivers are contained within a separate personal data capture device, the personal data is transferred from the personal data capture device to a microprocessor of the wireless communication device using an interface (e.g., an I2C bus) when the personal data capture device is attached to the wireless communication device. The microprocessor then stores the personal data in the memory.

At processing block 308, the personal data is transmitted from the wireless communication device to a network server over a wireless network. In one embodiment, the personal data is transmitted to the network server periodically. Alternatively, the personal data is transmitted upon receiving a user request.

At processing block 310, feedback information pertaining to the personal data is generated. As described above, the feedback information relates to the user's health and fitness activities and presents the user's personal data in the form of graphs, tables, map overlays, progressive charts, and comparisons with data of other users. In addition, the feedback information may include instructions provided by various specialists, such as fitness instructors, athletic trainers, diet or nutrition specialists, physicians, or any other fitness or health specialists.

At processing block 312, the feedback information is displayed to the user. In one embodiment, the feedback information is displayed on the user's web site which can be accessed from any client device (e.g., a personal computer). Alternatively, a display of the wireless communication device (e.g., a cellular phone display) is used to access the feedback information. In one embodiment, the display of the wireless communication device is also used to display specific portions of the user's personal data, e.g., the number of steps counted during the user's fitness activity or during the day, the distance walked by the user during the day, the amount of calories burned by the user during the day, etc.

Figure 4:
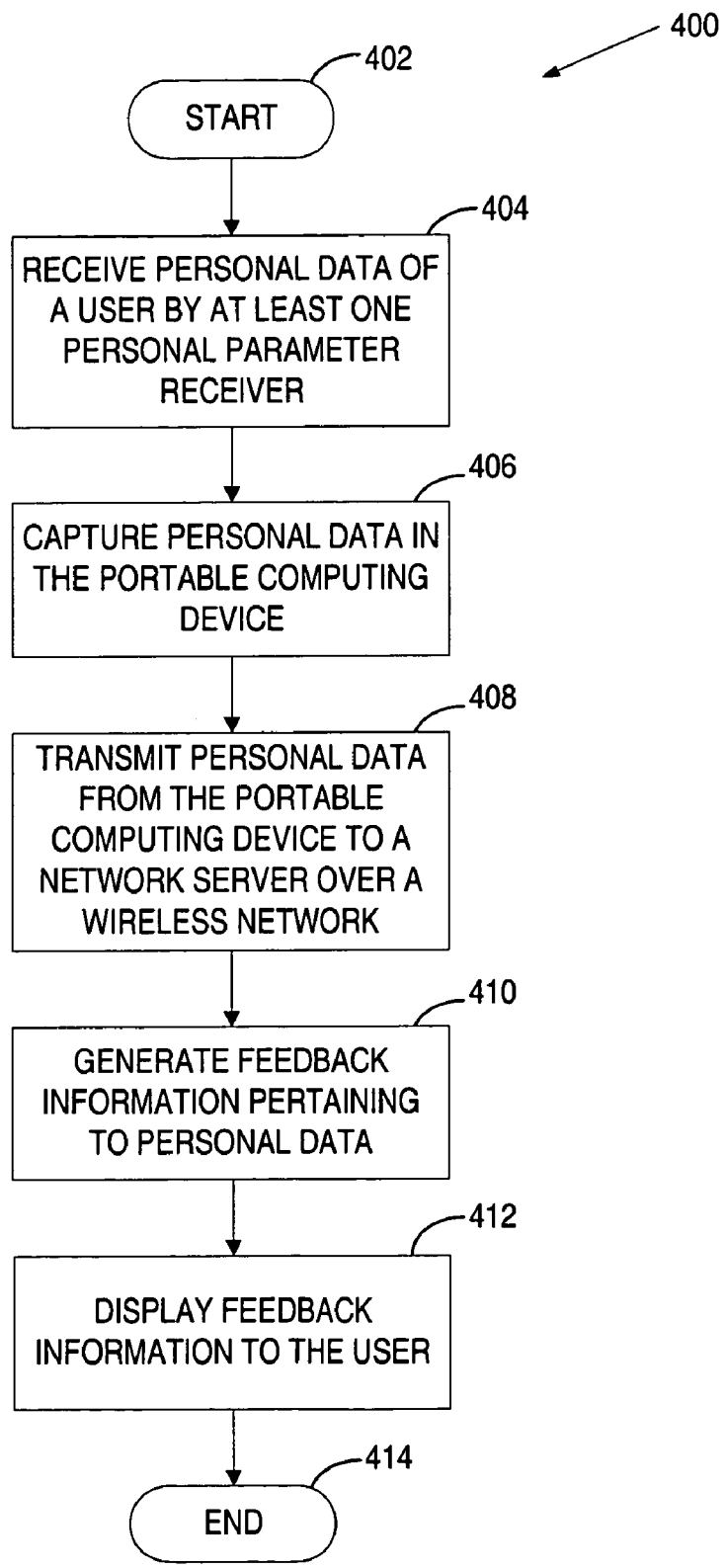
FIG. 4 is a flow diagram of a method for integrating personal data capturing functionality into a portable computing device, according to one embodiment of the present invention.

FIG. 4 is a flow diagram of a method for integrating personal data capturing functionality into a portable computing device, according to one embodiment of the present invention. At processing block 404, user's personal data is received by one or more personal parameter receivers. In one embodiment, the personal parameter receivers are contained in a separate personal data capture device which is attachable to a portable computing device. Alternatively, the personal parameter receivers are a part of the portable computing device. The portable computing device may be, for example, a PDA, a palmtop computer, or any other hand-held computing device. In one embodiment, the portable computing device is combined with a wireless communication device (e.g., a combination of a PDA and a cellular phone).

At processing block 406, the personal data collected by the personal parameter receivers is captured in the portable computing device. In one embodiment, in which the personal parameter receivers are a part of the portable computing device, the personal data is captured in the portable computing device by directly sending the personal data to a microprocessor which then stores it in memory. Alternatively, the personal data is transferred from the personal data capture device to a microprocessor of the portable computing device using an interface (e.g., an I2C bus) when the personal data capture device is attached to the portable computing device.

At processing block 408, the personal data is transmitted from the portable computing device to a network server over a wireless network either periodically or upon receiving a user request. Further, feedback information pertaining to the personal data is generated (processing block 410) and then displayed to the user (processing block 412). In one embodiment, the feedback information is displayed on the user's web site which can be accessed from any client device (e.g., a personal computer). Alternatively, a display of the portable computing device (e.g., a PDA display) can be used to access the feedback information. In one embodiment, the display of the portable computing device can also display specific portions of the user's personal data, e.g., the number of steps counted during the user's fitness activity or during the day, the distance walked by the user during the day, the amount of calories burned by the user during the day, etc.

Figure 5:
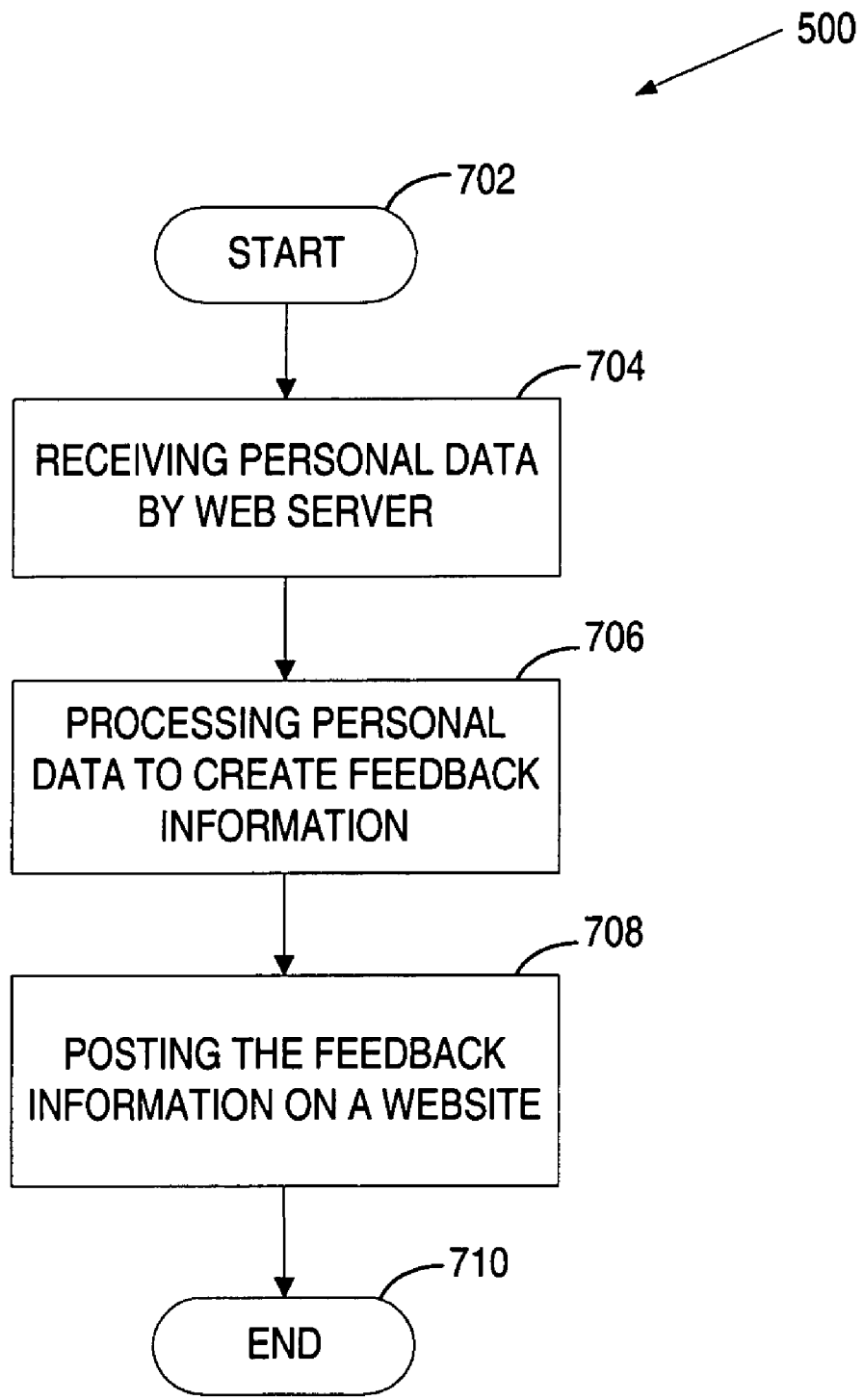
FIG. 5 is a flow diagram of one embodiment for posting personal data of a user on a web site.

FIG. 5 is a flow diagram of one embodiment for posting personal data of a user (also referred to herein as a subscriber) on a web site. Referring to FIG. 5, at processing block 704, network server 122 receives personal data of subscribers. In one embodiment, the personal data may be received from a plurality of personal data capture devices. The personal data may comprise physical data and biometrical parameters of each subscriber. The personal data may be stored in a repository of personal data which resides either directly on network server 122 or on a separate computer accessible by network server 122.

In one embodiment, the personal data of the subscriber is stored in the repository of personal data only if the subscriber maintains an account registered with network server 122. The account may be registered at any time before or simultaneously with first transmission of subscriber's personal data. At the time of creating the account, the subscriber may be required to provide a password or a code to prevent access to the personal data by anyone other than the subscriber. In one embodiment, the account information may be stored together with the personal data in the repository of the personal data. Alternatively, the account information may be stored in a separate database or file.

At processing block 706, the personal data is processed to create feedback information. Depending on the services selected by the subscriber, various feedback information may be created in response to the subscriber's personal data. In one embodiment, a fitness instructor, an athletic trainer, a diet or nutrition specialist, a physician, or any other fitness or health specialist may be able to access the subscriber's personal data. One or more fitness or health specialists may analyze the personal data and create the feedback information. In alternate embodiments, the personal data or its portion may be analyzed by a software program which may either create the feedback information entirely or assist fitness or health specialists in creating the feedback information. The feedback information may be stored either in the repository of personal data or in a separate database residing on network server 122 or on a different computer accessible by network server 122.

At processing block 708, the feedback information is posted on a web site. As described above, the web site may be a personal web site of the subscriber or a company web site that can be accessed by all subscribers. In one embodiment, the personal data may be posted on the web site in various forms such as graphs, tables and map overlays. In addition, the subscriber's personal data may be compared with personal data of other subscribers or with this subscriber's history data. In one embodiment, when the personal web site is used, the web site may be specifically created as a part of services provided to the subscriber. Alternatively, the subscriber's existing web site may be used for posting the feedback information and the personal data of the subscriber. In yet another embodiment, the feedback information and personal data may be posted on a company web site known to all subscribers. In either embodiment, access to the feedback information and personal data is protected either by a password or other means for maintaining confidentiality of personal information.

Several variations in the implementation of the methods and systems for integrating personal data capturing functionality into a wireless communication device and a portable computing device have been described. The specific arrangements and methods described herein are illustrative of the principles of this invention. Numerous modifications in form and detail may be made by those skilled in the art without departing from the true spirit and scope of the invention. Although this invention has been shown in relation to particular embodiments, it should not be considered so limited. Rather it is limited only by the appended claims.

What is claimed is:

1. A method for integrating personal data capturing functionality into a wireless communication device and for analyzing and supplying feedback information to a user, the method comprising:
   receiving personal data of said user by at least one personal parameter receiver, the personal data comprising step data corresponding to a number of steps counted during an activity of said user;
   capturing the personal data in the wireless communication device;
   periodically transmitting the personal data from the wireless communication device to a network server over a wireless network;
   at the network server, storing in a repository of personal data maintained by, or accessible from, the network server, the personal data from said user;
   at the network server, analyzing the personal data to generate feedback information for said user;
   at the network server, posting the feedback information to a web site that is accessible to said user;
   wherein said receiving, capturing, periodically transmitting, storing, analyzing and posting are performed with respect to personal data for each of a plurality of users received from their corresponding wireless communication devices, and wherein said analyzing further comprises comparing personal data for said user with personal data for at least one other different user from the received personal data from said plurality of users, and wherein posting comprises posting comparisons between the personal data of said user and personal data for said at least one other different user.

2. The method of claim 1 wherein the at least one personal parameter receiver is contained in a personal data capture device attachable to the wireless communication device.

3. The method of claim 1 wherein the at least one personal parameter receiver is contained in the wireless communication device.

4. The method of claim 1 wherein analyzing comprises analyzing the personal data according to health and/or fitness of said user such that the feedback information comprises information pertaining to health or fitness of said user.

5. The method of claim 1 wherein posting comprises posting the feedback information and the personal data in a form comprising one or more of: graphs, charts, tables and map overlays.

6. The method of claim 1 wherein analyzing further comprises generating for presentation to said user in the feedback information instructions from one or more of: a fitness instructor, physician, athletic trainer, nutritionist.

7. The method of claim 1 wherein posting comprises posting the feedback information to a web site that is accessible by said plurality of users.

8. The method of claim 1 wherein posting comprises posting the feedback information and the personal data of said user to a personal web site of said user.

9. A method for integrating personal data capturing functionality into a portable computing device and for analyzing and supplying feedback information to a user, the method comprising:
   receiving personal data of said user by at least one personal parameter receiver, the personal data comprising step data corresponding to a number of steps counted during an activity of said user;
   capturing the personal data in the portable computing device;
   periodically transmitting the personal data from the portable computing device to a network server over a wireless network;
   at the network server, storing in a repository of personal data maintained by, or accessible from, the network server, personal data from said user;
   at the network server, analyzing the personal data to generate feedback information for said user; and
   at the network server, posting the feedback information to a web site that is accessible to said user;
   wherein said receiving, capturing, periodically transmitting, storing, analyzing and posting are performed with respect to personal data for each of a plurality of users received from their corresponding wireless communication devices, and wherein said analyzing further comprises comparing personal data for said user with personal data for at least one other different user from the received personal data from said plurality of users, and wherein posting comprises posting comparisons between the personal data of said user and personal data for said at least one other different user.

10. The method of claim 9 wherein the at least one personal parameter receiver is contained in a personal data capture device attachable to the portable computing device.

11. The method of claim 9 wherein the at least one personal parameter receiver is contained in the portable computing device.

12. The method of claim 9 wherein analyzing comprises analyzing the personal data according to health and/or fitness of said user such that the feedback information contains information pertaining to health or fitness of said user.

13. The method of claim 9 wherein posting comprises posting the feedback information and the personal data in a form comprising one or more of: graphs, charts, tables and map overlays.

14. The method of claim 9 wherein analyzing further comprises generating for presentation to said user in the feedback information instructions from one or more of: a fitness instructor, physician, athletic trainer and nutritionist.

15. The method of claim 9 wherein posting comprises posting the feedback information to a web site that is accessible by said plurality of users.

16. The method of claim 9, wherein posting comprises posting the feedback information and the personal data of said user to a personal web site of said user.

* * * * *